United States Patent
Nirchio

(10) Patent No.: US 6,232,503 B1
(45) Date of Patent: May 15, 2001

(54) ALKYNYL ARYL SULFONES

(75) Inventor: Peter C. Nirchio, Lebanon, NJ (US)

(73) Assignee: Lonza Inc., Fair Lawn, NJ (US)

( * ) Notice: Subject to any disclaimer, the term of this patent is extended or adjusted under 35 U.S.C. 154(b) by 0 days.

(21) Appl. No.: 09/400,654

(22) Filed: Sep. 21, 1999

Related U.S. Application Data

(60) Provisional application No. 60/125,290, filed on Mar. 19, 1999.

(51) Int. Cl.[7] .................... C07C 315/04; C07C 317/08
(52) U.S. Cl. .................... 568/28; 568/30; 568/31; 568/29; 568/33
(58) Field of Search .................... 568/28, 29, 30, 568/31, 33; 564/44

(56) References Cited

U.S. PATENT DOCUMENTS

| | | | |
|---|---|---|---|
| 3,267,150 | 8/1966 | Moore et al. | 260/607 |
| 3,777,024 | 12/1973 | Martin et al. | 205/70 |
| 4,335,142 | 6/1982 | Relyea et al. | 424/337 |
| 4,559,082 | 12/1985 | Felix et al. | 71/98 |
| 4,851,423 | 7/1989 | Girijavallabhan et al. | 514/399 |

FOREIGN PATENT DOCUMENTS

| | | |
|---|---|---|
| 28150 | 3/1970 | (ZA) . |

OTHER PUBLICATIONS

Williamson, et al., J. Am. Chem. Soc. 115(7):2590–7, 1993 (abstract).

Otten et al., Eur. J. Org. Chem.9:1997–2001, 1998 (abstract).

Banchero, J.T., (1959) Chemical Abstracts, vol. 53: 5112(e).

Abstract of Bhattacharya, S.N., et al., Organometal. Chem. Syn (1971) 1(2), pp. 145–9.

Abstract of Villenave, J.J., et al., Calorim. Anal Therm. (1990), pp. 20–21, 227–33.

Abstract of Chen, Z. et al., Synth. Commun., (1994) vol. 24 (21), pp. 3149–55.

Abstract of Tykwinski, R. et al., J. Org. Chem (1993) vol. 58 (19), pp. 5235–7.

Abstract of Waykole, L. et al., Org. Synth. (1989) vol. 67, pp. 149–56.

CA:114:229441 abs of Calorim Anal Therm by Villenave et al 20–21 pp 227–33, 1990.*

CA:78:110776 abs of Ann Chim (Paris) by Gorgues 7(4) pp 221–21, 1972.*

CA: 106:156187 abs of Chem Ber by Kosack 120(1) pp 71–77, 1987.*

Chemical Abstracts of vol. 54 10928g, Jun. 1960.*

CA:122:55669 abs of Synth Commun by Chen et al 24(21) pp 3149–55, 1994.*

CA:131:44984 abs of J Chem Soc Perkins Trans 1 by Zhang (6) pp 675–6, 1999.*

CA:75:36214 abs of Organometal Chem Syn by Bhattacharya 1(2) pp 145–9, 1971.*

\* cited by examiner

Primary Examiner—Jean F Vollano
(74) Attorney, Agent, or Firm—Darby & Darby

(57) ABSTRACT

The present invention provides compounds having the formula

I

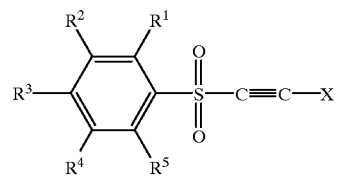

wherein $R^1$, $R^2$, $R^3$, $R^4$, and $R^5$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$, alkyl, hydroxyl, thiol, —CN, —$CF_3$, —$OCF_3$, —$NO_2$, acetyl, or —$NR^6R^7$; $R^6$ and $R^7$ are independently hydrogen, methyl, or ethyl; and X is iodine or bromine. Another embodiment of the invention includes specific ethynyl benzene sulfone derivatives. The alkynyl aryl sulfones of the present invention are useful as biocides, including, but not limited to, bactericides, fungicides, and preservatives. Also, a method of preparing the halogenated alkynyl aryl sulfones of formula I is provided. The method comprises contacting an alkynyl aryl sulfone with N-iodosuccinamide or N-bromosuccinamide, acetone, and silver nitrate to form the corresponding halogenated alkynyl aryl sulfone.

45 Claims, No Drawings

ALKYNYL ARYL SULFONES

This patent application claims the priority of U.S. provisional patent application No. 60/125,290, filed Mar. 19, 1999, which is incorporated herein by reference.

FIELD OF THE INVENTION

This invention relates to alkynyl aryl sulfones and the use of such compounds as biocides.

BACKGROUND OF THE INVENTION

Aryl sulfones are known to be effective as herbicides and plant growth regulators. See, for example, U.S. Pat. Nos. 4,335,142; 4,559,082; and 3,267,150.

Moore et al., U.S. Pat. No. 3,267,150, discloses haloalkenyl sulfones useful as agricultural products, such as germicides and fungicides.

Felix et al., U.S. Pat. No. 4,559,082, describes herbicidal compositions comprising an herbicidally effective amount of a thiocarbamate and an amount of an unsaturated aryl sulfide, sulfoxide, or sulfone sufficient to extend the soil life of the thiocarbamate.

Although there are numerous biocidal compositions on the market, there is a continuing need for neutral compositions with high biocidal efficacy.

SUMMARY OF THE INVENTION

Applicants have discovered alkynyl aryl sulfones having high biocidal activity. These compounds are useful as biocides, including, but not limited to, bactericides, fungicides, and preservatives. Applicants have also discovered that haloalkynyl aryl sulfones may be prepared by reacting the corresponding non-halogenated alkynyl aryl sulfone with N-iodosuccinamide or N-bromosuccinamide, acetone, and silver nitrate.

Biocidal compositions comprising a microbiocidally effective amount of one or more of the alkynyl aryl sulfones are a further embodiment of the present invention.

Still another embodiment is a method of controlling microorganisms comprising applying an effective amount of one or more alkynyl aryl sulfones to the microorganisms.

DETAILED DESCRIPTION OF THE INVENTION

The present invention encompasses halogenated alkynyl aryl sulfones having formula I below:

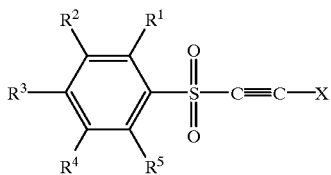

I where $R^1$, $R^2$, $R^3$, $R^4$, and $R^5$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —$CF_3$, —$OCF_3$, —$NO_2$, acetyl, or —$NR^6R^7$; $R^6$ and $R^7$ are independently hydrogen, methyl, or ethyl; and X is iodine or bromine. $R^1$ and $R^2$ are preferably hydrogen.

Preferably, at least two of $R^3$, $R^4$, and $R^5$ are hydrogen and X is iodine. More preferably, two of $R^3$, $R^4$, and $R^5$ are hydrogen and the third group is hydrogen, chlorine, bromine, fluorine, iodine, methyl, ethyl, methoxy, ethoxy, n-propoxy, iso-propoxy, thiomethoxy, thioethoxy, n-thiopropoxy, iso-thiopropoxy, linear or branched $C_1$–$C_8$ alkyl, —$CF_3$, or —$NO_2$. Most preferably, two of $R^3$, $R^4$, and $R^5$ are hydrogen and the third group is hydrogen, chlorine, bromine, fluorine, iodine, methyl, ethyl, methoxy, ethoxy, n-propoxy, or iso-propoxy.

Examples of preferred compounds of formula I include, but are not limited to, iodoethynyl 4-methylbenzene sulfone; iodoethynyl 4-methoxybenzene sulfone; iodoethynyl 4-thiomethoxybenzene sulfone; iodoethynyl 4-t-butylbenzene sulfone; iodoethynyl 4-ethylbenzene sulfone; iodoethynyl 4-trifluoromethoxybenzene sulfone; iodoethynyl 2,4,6-trimethylbezene sulfone; iodoethynyl 3,4-dimethoxybenzene sulfone; and iodoethynyl benzene sulfone. Examples of more preferred compounds of formula I include, but are not limited to, iodoethynyl 4-methylbenzene sulfone, iodoethynyl 4-ethylbenzene sulfone, and iodoethynyl 4-methoxybenzene sulfone.

Another embodiment of the present invention encompasses alkynyl aryl sulfones having formula II below:

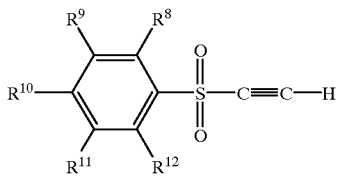

II where $R^8$, $R^9$, $R^{10}$, $R^{11}$, and $R^{12}$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —$CF_3$, —$OCF_3$, —$NO_2$, acetyl, or —$NR^{13}R^{14}$; $R^{13}$ and $R^{14}$ are independently hydrogen, methyl, or ethyl; and at least one of $R^8$, $R^9$, $R^{10}$, $R^{11}$, and $R^{12}$ is not hydrogen or methyl; with the proviso that $R^{10}$ is fluorine, iodine, ethoxy, substituted or unsubstituted n-propoxy, substituted or unsubstituted iso-propoxy, substituted or unsubstituted linear or branched $C_1$–$C_3$ thioalkoxy, substituted or unsubstituted ethyl, substituted or unsubstituted linear or branched $C_3$–$C_8$, alkyl, hydroxyl, thiol, —CN, —$CF_3$, —$OCF_3$, acetyl, or —$NR^{13}R^{14}$ when $R^8$, $R^9$, $R^{11}$, and $R^{12}$ are hydrogen. $R^8$ and $R^9$ are preferably hydrogen. When $R^8$, $R^9$, and $R^{10}$ are hydrogen, preferably, one of $R^{11}$ and $R^{12}$ is hydrogen and the other is chlorine, bromine, fluorine, iodine, methoxy, ethoxy, n-propoxy, iso-propoxy, thiomethoxy, thioethoxy, n-thiopropoxy, or iso-thiopropoxy. When $R^8$, $R^9$, $R^{11}$, and $R^{12}$ are hydrogen, $R^{10}$ is preferably fluorine, iodine, ethoxy, n-propoxy, iso-propoxy, thiomethoxy, thioethoxy, n-thiopropoxy, or iso-thiopropoxy.

Examples of preferred compounds of formula II include, but are not limited to, ethynyl 4-t-butylbenzene sulfone; ethynyl 4-thiomethoxybenzene sulfone; ethynyl 4-ethylbenzene sulfone; ethynyl 4-trifluoromethoxybenzene sulfone; and ethynyl 3,4-dimethoxybenzene sulfone.

The invention also encompasses alkynyl aryl sulfones having formula III below:

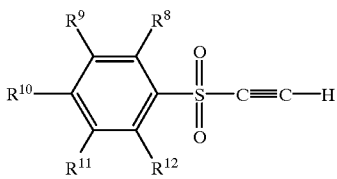

wherein $R^8$, $R^9$, $R^{10}$, $R^{12}$, and $R^{11}$ are independently hydrogen or methyl and at least two of $R^8$, $R^9$, $R^{10}$, $R^{11}$, and $R^{12}$ are methyl; with the proviso that $R^8$ is not methyl when $R^9$ and $R^{11}$ are hydrogen and $R^{10}$ and $R^{12}$ are methyl.

Another embodiment of the invention is a biocidal concentrate comprising from about 1 to about 15%, preferably from about 1 to about 5%, by weight of one or more alkynyl aryl sulfones having the formula

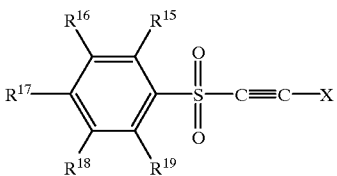

where $R^{15}$, $R^{16}$, $R^{17}$, $R^{18}$, and $R^{19}$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —CF$_3$, —OCF$_3$, —NO$_2$, acetyl, or —NR$^{20}$R$^{21}$; R$^{20}$ and R$^{21}$ are independently hydrogen, methyl, or ethyl; and X is hydrogen, iodine, or bromine, based upon 100% weight of total concentrate. The compounds of formula IV include, but are not limited to, the aforementioned compounds of formulas I, II, and III; ethynyl p-tolyl sulfone; ethynylbenzene sulfone; ethynyl 4-methoxybenzene sulfone; ethynyl 4-n-hexoxybenzene sulfone; ethynyl 4-nitrobenzene sulfone; ethynyl 4-chlorobenzene sulfone; ethynyl 4-bromobenzene sulfone; ethynyl 2-methylbenzene sulfone; ethynyl 3-methylbenzene sulfone; and ethynyl 2,4,6-trimethylbenzene sulfone. Preferred alkynyl sulfones incorporated in the biocidal concentrate include, but are not limited to, ethynyl 4-methylbenzene sulfone, ethynyl 4-methoxybenzene sulfone, iodoethynyl 4methylbenzene sulfone, iodoethynyl 4-methoxybenzene sulfone, and combinations thereof. Biocides are materials that prevent the growth of, inhibit the growth of, or kill microorganisms, including, but not limited to, bacteria and fungi. Interestingly, the halogenated haloalkynyl aryl sulfones of the present invention remain biocidally effective even after cursory decomposition, i.e., loss of the halogen.

Generally, the biocidal concentrate further comprises from about 1 to about 10%, preferably from about 1 to about 5%, by weight of a solid or liquid formulation adjuvant and up to 15%, preferably from about 0.5 to 10%, by weight of one or more surfactants, based upon 100% weight of total biocidal concentrate.

The compositions may also comprise further auxiliaries, such as wetting agents, adhesives, emulsifiers, preservatives, fillers, carriers, viscosity and pH regulators, binders, tackifiers, fertilizers, other active ingredients, and any combination of any of the foregoing. Other conventional adjuvants may be added to the composition for different applications as known to those of ordinary skill in the art.

The alkynyl aryl sulfones may be incorporated into different formulations including, but not limited to, granules, pellets, tablets, wettable powders, wettable dusts, microencapsulated materials, impregnated materials, emulsifiable concentrates, flowable concentrates, soluble concentrates, and ready-to-use solutions. The concentrates, granules, pellets, tablets, dusts, and other materials may be diluted with a solvent, such as water, to form a use dilution of the alkynyl aryl sulfones which may be used as a biocide, such as a bactericide, fungicide, herbicide, or preservative. The use dilution comprises a microbiocidally, bactericidally, or fungicidally effective amount of one or more of the alkynyl aryl sulfones. Generally, the use dilution comprises from about 0.0005 to about 5%, preferably from about 0.001 to about 0.1%, by weight of the alkynyl aryl sulfones based upon 100% weight of total use dilution.

Examples of compositions which may contain the alkynyl aryl sulfones of the present invention include, but are not limited to, personal care products, such as shampoos; wood treatment products; paper products; water treatment equipment; and the like.

Also, the invention includes a method of controlling microorganisms, including bacteria and fungi, comprising applying a microbiocidally, bactericidally, or fungicidally effective amount of one or more of the alkynyl aryl sulfones of formula IV to the microorganisms.

The non-halogenated alkynyl aryl sulfones of formulas II and III above may be prepared by methods known in the art, such as those in Bhattacharya, S. N. et al., *Organometal. Chem. Syn.*, 1:145–149 (1970/1971). One method of preparing such sulfones comprises reacting a mixture of potassium carbonate and sodium bicarbonate in water with trimethylsilylalkynyl aryl sulfone in methanol to yield the corresponding alkynyl aryl sulfone. The trimethylsilylalkynyl aryl sulfone has the formula

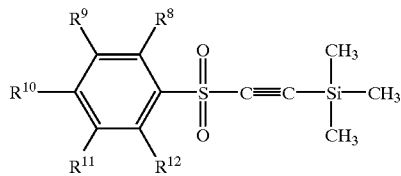

where $R^8$, $R^9$, $R^{10}$, $R^{11}$, and $R^{12}$ are defined as in formulas II and III.

Trimethylsilylalkynyl aryl sulfones may be prepared by methods well known in the art, such as those described in Waykole, L. et al., *Organic Synthesis*, 67:149 (1988). One method of preparing trimethylsilylalkynyl aryl sulfones comprises reacting bis(trimethylsilyl)acetylene with a benzenesulfonyl chloride having the formula:

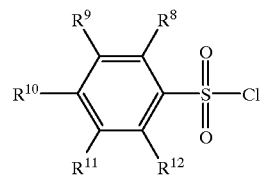

where $R^8$, $R^9$, $R^{10}$, $R^{11}$, and $R^{12}$ are defined as in formulas II and III., to yield the corresponding alkynyl aryl sulfone.

The haloalkynyl aryl sulfones of formula I may be prepared by halogenating the corresponding non-halogenated alkynyl aryl sulfones, i.e., compounds of formula I when X is hydrogen. For example, the non-halogenated alkynyl aryl sulfones may be iodinated or brominated by reacting the non-halogenated alkynyl aryl sulfone with N-iodosuccinamide or N-bromosuccinamide, acetone, and silver nitrate to yield the corresponding halogenated alkynyl aryl sulfone.

DESCRIPTION OF THE PREFERRED EMBODIMENTS

The following examples illustrate the invention without limitation. All parts and percentages are given by weight unless otherwise indicated.

EXAMPLE 1

Preparation of Ethynyl 4-Methoxybenzene Sulfone 5 g of 4-methoxybenzenesulfonyl chloride (24.195 mmole) available from Aldrich Chemical Co. of Milwaukee, Wis., 50 mL of dichloromethane, and 3.55 g of silver trichloride (26.615 mmole) were added to a 300 mL schlenk tube. The mixture was stirred at room temperature for 30 minutes.

4.535 g of bis(trimethylsilyl)acetylene (BTMSA) (26.615 mmole) available from Aldrich Chemical Co. and 50 mL of dichloromethane were added to a jacketed 100 mL three-necked flask. The mixture was stirred to dissolve the BTMSA in the dichloromethane. A drying tube, 60 mL addition funnel, and thermometer were fitted to the flask. The flask was then cooled to 5° C.

The mixture in the schlenk tube was transferred into the addition funnel on the flask under $N_2$ pressure with a Teflon tube having a piece of filter paper wired to one end of the Teflon tube. The mixture in the addition funnel was added to the flask over a period of 1 hour to maintain the temperature in the flask at about 5° C. After the addition, the flask was allowed to warm to room temperature. The mixture was stirred for 16 hours.

A slurry was formed by mixing 100 mL of ice with 100 mL of 20% hydrogen chloride. The mixture in the flask was poured into the slurry and stirred until the ice melted. The mixture was added to a separatory funnel to separate the organic layer from the aqueous layer. The aqueous layer was washed twice with 100 mL of dichloromethane. The organic layers were combined and dried over anhydrous magnesium sulfate. The anhydrous magnesium sulfate was filtered away and the solution evaporated under vacuum to yield a residue. Hexanes available from J. T. Baker of Philipsburg, N.J., were heated until boiling. The residue was then dissolved in approximately 40 mL of the heated hexanes. The hexane solution was allowed to cool overnight in a freezer to yield white crystals (4.34 g, 66.9% yield) of trimethylsilylethynyl 4-methoxybenzene sulfone.

4.3 g of trimethylsilylethynyl 4-methoxybenzene sulfone (16.02 mmole) and 30 mL of methanol were added to a 100 mL single necked recovery flask. The methanol solution was stirred until it became homogeneous. An aqueous buffer solution containing 50 mL of water, 0.072 g of potassium carbonate (0.52 mmole), and 0.044 g of sodium bicarbonate (0.52 mmole) was added dropwise over 15 minutes to the methanol solution in order to maintain the temperature of the methanol solution between 25 and 35° C. 30 minutes after the addition of the aqueous buffer solution, the methanol solution was added to a separatory funnel with 100 mL of chloroform and shaken to separate the aqueous phase and the chloroform phase. The aqueous phase was washed with 100 mL of chloroform. The chloroform layers were combined and dried over magnesium sulfate. The chloroform solution was filtered to remove the magnesium sulfate and evaporated under vacuum to yield a residue. The residue was taken up in a minimum of ethyl acetate and layered with an equal volume of hexanes. The solution was stored in a freezer maintained at −15° C. overnight to yield white crystals (2.72 g, 86.6% yield) of ethynyl 4-methoxybenzene sulfone.

EXAMPLE 2

Preparation of Iodoethynyl 4-Methoxybenzene Sulfone 1.0 g of ethynyl 4-methoxybenzene sulfone (5.096 mmole) as prepared in Example 1, 1.169 g of N-iodosuccinamide (5.1979 mmole) available from Aldrich Chemical Co., and 20 mL of acetone were added to a 100 mL recovery flask. The mixture was stirred until all of the solids were dissolved. 0.104 g of silver nitrate (0.6115 mmole) was added to the mixture and stirred while a white precipitate formed. After one hour, the mixture was filtered to remove the precipitate. The mixture was evaporated under vacuum to form an oily residue. The residue was chromatographed on silica gel using a dichloromethane/ethyl acetate eluant having a 5:1 volume ratio. The fractions on the silica gel containing product were evaporated under vacuum to yield a white solid (1.387 g, 84.5% yield) of iodoethynyl 4-methoxybenzene sulfone.

EXAMPLE 3

Preparation of Iodoethynyl 4-Methylbenzene Sulfone

Iodoethynyl 4-methylbenzene sulfone was prepared by the procedure in Examples 1 and 2, except that a molar equivalent of 4-methylbenzenesulfonyl chloride available from Aldrich Chemical Co. was substituted for 4-methoxybenzenesulfonyl chloride.

EXAMPLE 4

Preparation of Ethynyl 4-t-Butylbenzene Sulfone

Ethynyl 4-t-butylbenzene sulfone was prepared as described in Example 1 except 4-t-butylbenzenesulfonyl chloride was substituted for 4-methoxybenzenesulfonyl chloride.

EXAMPLE 5

Preparation of iodoethynyl 4-t-Butylbenzene Sulfone

Iodoethynyl 4-t-butylbenzene sulfone was prepared as described in Example 2 except ethynyl 4-t-butylbenzene sulfone as prepared in Example 4 was substituted for ethynyl 4-methoxybenzene sulfone.

EXAMPLE 6

Preparation of Ethynyl 4-Ethylbenzene Sulfone

Ethynyl 4ethylbenzene sulfone was prepared as described in Example 1 except 4-ethylbenzenesulfonyl chloride was substituted for 4-methoxybenzenesulfonyl chloride.

EXAMPLE 7

Preparation of Iodoethynyl 4-Ethylbenzene Sulfone

Iodoethynyl 4-ethylbenzene sulfone was prepared as described in Example 2 except ethynyl 4-ethylbenzene sulfone as prepared in Example 6 was substituted for ethynyl 4-methoxybenzene sulfone.

EXAMPLE 8

Preparation of Ethynyl 4-Trifluoromethoxybenzene Sulfone

Ethynyl 4-trifluoromethoxybenzene sulfone was prepared as described in Example 1 except 4-trifluoromethoxybenzenesulfonyl chloride was substituted for 4-methoxybenzenesulfonyl chloride.

EXAMPLE 9

Preparation of Iodoethynyl 4-Trifluoromethoxybenzene Sulfone

Iodoethynyl 4-trifluoromethoxybenzene sulfone was prepared as described in Example 2 except ethynyl 4-trifluoromethoxybenzene sulfone as prepared in Example 8 was substituted for ethynyl 4-methoxybenzene sulfone.

EXAMPLE 10

Preparation of Ethynyl 2,4,6-Trimethylbenzene Sulfone

Ethynyl 2,4,6-trimethylbenzene sulfone was prepared as described in Example 1 except 2,4,6-trimethylbenzenesulfonyl chloride was substituted for 4-methoxybenzenesulfonyl chloride.

EXAMPLE 11

Preparation of Iodoethynyl 2,4,6-Trimethylbenzene Sulfone

Iodoethynyl 2,4,6-trimethylbenzene sulfone was prepared as described in Example 2 except ethynyl 2,4,6-trimethylbenzene sulfone as prepared in Example 10 was substituted for ethynyl 4-methoxybenzene sulfone.

EXAMPLE 12

Preparation of Ethynyl 3,4-Dimethoxybenzene Sulfone

Ethynyl 3,4-dimethoxybenzene sulfone was prepared as described in Example 1 except 3,4-dimethoxybenzenesulfonyl chloride was substituted for 4-methoxybenesulfonyl chloride.

EXAMPLE 13

Preparation of Iodoethynyl 3,4-Dimethoxybenzene Sulfone

Iodoethynyl 3,4-dimethoxybenzene sulfone was prepared as described in Example 2 except ethynyl 3,4-dimethoxybenzene sulfone as prepared in Example 12 was substituted for ethynyl 4-methoxybenzene sulfone.

EXAMPLE 14

Preparation of Ethynyl Benzene Sulfone

Ethynyl benzene sulfone was prepared as described in Example 1 except benzenesulfonyl chloride was substituted for 4-methoxybenzenesulfonyl chloride.

EXAMPLE 15

Preparation of Iodoethynyl Benzene Sulfone

Iodoethynyl benzene sulfone was prepared as described in Example 2 except ethynyl benzene sulfone as prepared in Example 14 was substituted for ethynyl 4-methoxybenzene sulfone.

EXAMPLE 16

The minimum inhibitory concentrations of ethynyl 4-methylbenzene sulfone, available from Aldrich Chemical Co., and the sulfones prepared in Examples 1–15 were determined against the bacteria *Burkholderia cepacia* and *Staphylococcus aureus* by the zone of inhibition assay method common in the art. *Burkholderia cepacia* and *Staphylococcus aureus* was contacted with each sulfone for 24 hours in a Day-Engley neutralizing media (Difco Manual, $10^{th}$ Ed., p. 261–263 (1984). The results are shown in Table 1.

TABLE 1

| Alkynyl Aryl Sulfone | 24 Hour Minimum Inhibitory Concentration (mg/L) | |
| --- | --- | --- |
| | Burkholderia cepacia | Staphlococcus aureus |
| Ethynyl 4-Methylbenzene Sulfone | 100–300 | 3–10 |
| Iodoethynyl 4-Methylbenzene Sulfone | 0.3–1 | 0.3–1 |
| Ethynyl 4-Methoxybenzene Sulfone | 30–100 | 1–3 |
| Iodoethynyl 4-Methoxybenzene Sulfone | 30–100 | 3–10 |
| Ethynyl 4-t-Butylbenzene Sulfone | >1,000 | 30–100 |
| Iodoethynyl 4-t-Butylbenzene Sulfone | 300–1,000 | 1–3 |
| Ethynyl 4-Ethylbenzene Sulfone | 300–1,000 | 3–10 |
| Iodoethynyl 4-Ethylbenzene Sulfone | 100–300 | 0.3–1 |
| Ethynyl 4-Trifluoromethoxybenzene Sulfone | >1,000 | 3–10 |
| Iodoethynyl 4-Trifluoromethoxybenzene Sulfone | 100–300 | 0.3–1 |
| Ethynyl 2,4,6-Trimethylbenzene Sulfone | 300–1,000 | 300–1,000 |
| Iodoethynyl 2,4,6-Trimethylbenzene Sulfone | 300–1,000 | 100–300 |
| Ethynyl 3,4-Dimethoxybenzene Sulfone | >1,000 | 10–30 |
| Iodoethynyl 3,4-Dimethoxybenzene Sulfone | 300–1,000 | 30–100 |
| Ethynyl Benzene Sulfone | 10–30 | 1–3 |
| Iodoethynyl Benzene Sulfone | 3–10 | 0.3–1 |

EXAMPLE 17

The minimum inhibitory concentrations of ethynyl 4-methylbenzene sulfone and the sulfones prepared in Examples 1–15 were determined against the fungi *Aspergillus niger* by the zone of inhibition assay method common in the art. *A. niger* ATCC #16404 was contacted with each sulfone for 5 days in a Day-Engley neutralizing media. The results are shown in Table 2.

TABLE 2

| Alkynyl Aryl Sulfone | 5 Day Minimum Inhibitory Concentration *Aspergillus niger* (mg/L) |
| --- | --- |
| Ethynyl 4-Methylbenzene Sulfone | 3,000–10,000 |
| Iodoethynyl 4-Methylbenzene Sulfone | 100–300 |
| Ethynyl 4-Methoxybenzene Sulfone | 1,000–3,000 |
| Iodoethynyl 4-Methoxybenzene Sulfone | 30–100 |
| Ethynyl 4-t-Butylbenzene Sulfone | >10,000 |
| Iodoethynyl 4-t-Butylbenzene Sulfone | 100–300 |
| Ethynyl 4-Ethylbenzene Sulfone | 3,000–10,000 |
| Iodoethynyl 4-Ethylbenzene Sulfone | 10–30 |
| Ethynyl 4-Trifluoromethoxybenzene Sulfone | >10,000 |

TABLE 2-continued

| Alkynyl Aryl Sulfone | 5 Day Minimum Inhibitory Concentration *Aspergillus niger* (mg/L) |
|---|---|
| Iodoethynyl 4-Trifluoromethoxybenzene Sulfone | 30–100 |
| Ethynyl 2,4,6-Trimethylbenzene Sulfone | 3,000–10,000 |
| Iodoethynyl 2,4,6-Trimethylbenzene Sulfone | 100–300 |
| Ethynyl 3,4-Dimethoxybenzene Sulfone | >10,000 |
| Iodoethynyl 3,4-Dimethoxybenzene Sulfone | 300–1,000 |
| Ethynyl Benzene Sulfone | 1,000–3,000 |
| Iodoethynyl Benzene Sulfone | 300–1,000 |

EXAMPLE 18

A shampoo having a pH of about 7 and containing iodoethynyl-4-methoxybenzene sulfone was prepared having the formulation of Table 3 below.

TABLE 3

Iodoethynyl-4-methoxybenzene Sulfone Shampoo Formulation

| Ingredient | Parts (by weight) |
|---|---|
| Sodium Lauryl Ether Sulfate | 35.0 |
| Triethanolamine Lauryl Sulfate | 25.0 |
| Cocamide DEA | 3.0 |
| PolyPro 5000 ™ * (hydrolyzed collagen) | 1.0 |
| Sterile Deionized Water | 36.0 |
| 10.0% Citric Acid | 0.3 |
| Iodoethynyl-4-methoxybenzene Sulfone | 0.05 |
| Total | 100.35 |

*PolyPro 5000 ™ is available from Hormel & Co. of Austin, MN.

EXAMPLE 19

The bactericidal efficacy of the shampoo formulation containing iodoethynyl-4-methoxybenzene sulfone prepared in Example 18 was determined as follows. A mixture of 18 to 24 hour bacterial cultures of *Pseudomonas aeruginosa*, *Staphylococcus aureus*, and *Escherichia coli* was prepared. The shampoo was inoculated with the mixture of bacterial cultures and incubated at room temperature for 28 days. The number of colony forming units present in the shampoo after 0, 14, and 28 days was determined by neutralizing a small amount of the inoculated shampoo with Day-Engley neutralizing broth and adding serially diluted samples of the broth to soy agar plates. The plates were incubated for 48 hours.

This procedure was repeated with Glydrant Plus® Liquid available from Lonza Inc. of Annandale, N.J., as well as with the shampoo formulation prepared in Example 18 without iodoethynyl-4-methoxybenzene sulfone, i.e., a preservative free shampoo.

The results are shown in Table 4 below.

TABLE 4

| | Mixture of *Pseudomonas aeruginosa*, *Staphylococcus aureus*, and *Escherichia coli* (cfu/mL) | | |
|---|---|---|---|
| | Iodoethynyl-4- | Control | |
| Day | methoxybenzene Sulfone Shampoo | Glydant Plus ® Liquid | Preservative Free Shampoo |
| 0 | $7.0 \times 10^6$ | $6.5 \times 10^6$ | $5.5 \times 10^6$ |
| 14 | <10 | <10 | $5.0 \times 10^6$ |
| 28 | <10 | <10 | $3.2 \times 10^6$ |

EXAMPLE 20

The fungicidal efficacy of the shampoo formulation containing iodoethynyl-4-methoxybenzene sulfone prepared in Example 18 was determined as follows. A mixture of a 48 hour culture of *Candida albicans* and 7 to 14 day culture of *Aspergillus niger* was prepared. The shampoo was inoculated with the mixture of fungi and incubated at room temperature for 28 days. The number of colony forming units present in the shampoo after 0, 14, and 28 days was determined by neutralizing a small amount of the inoculated shampoo with Day-Engley neutralizing broth and adding serially diluted samples of the broth to dextrose agar plates. The plates were incubated for 3 to 5 days.

This procedure was repeated with Glydrant Pluse® Liquid available from Lonza Inc. of Annandale, N.J., as well as with the shampoo formulation prepared in Example 18 without iodoethynyl-4-methoxybenzene sulfone, i.e., a preservative free shampoo.

The results are shown in Table 5 below.

TABLE 5

| | Mixture of *Candida albicans* and *Aspergillus niger* (cfu/mL) | | |
|---|---|---|---|
| | Iodoethynyl-4- | Control | |
| Day | methoxybenzene Sulfone Shampoo | Glydant Plus ® Liquid | Preservative Free Shampoo |
| 0 | $1.3 \times 10^5$ | $1.0 \times 10^5$ | $1.3 \times 10^5$ |
| 14 | <10 | <10 | $7.0 \times 10^4$ |
| 28 | <10 | <10 | $6.0 \times 10^4$ |

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A compound having the formula

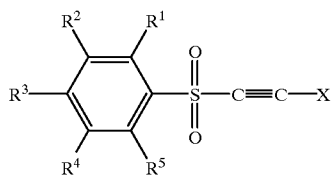

wherein $R^1$, $R^2$, $R^3$, $R^4$, and $R^5$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —$CF_3$, —$OCF_3$, —$NO_2$, acetyl, or —$NR^6R^7$; $R^6$ and $R^7$ are independently hydrogen, methyl, or ethyl; and X is iodine or bromine.

2. The compound of claim 1, wherein X is iodine.

3. The compound of claim 2, wherein $R^1$ and $R^2$ are hydrogen.

4. The compound of claim 3, wherein at least two of $R^3$, $R^4$, and $R^5$ are hydrogen.

5. The compound of claim 3, wherein $R^3$ and $R^4$ are hydrogen and $R^5$ is selected from the group consisting of hydrogen, chlorine, bromine, fluorine, iodine, methyl, ethyl, methoxy, ethoxy, n-propoxy, iso-propoxy, thiomethoxy, thioethoxy, n-thiopropoxy, and iso-thiopropoxy.

6. The compound of claim 3, wherein $R^3$ and $R^5$ are hydrogen and $R^4$ is selected from the group consisting of chlorine, bromine, fluorine, iodine, methyl, ethyl, methoxy, ethoxy, n-propoxy, iso-propoxy, thiomethoxy,thioethoxy, n-thiopropoxy, and iso-thiopropoxy.

7. The compound of claim 3, wherein $R^4$ and $R^5$ are hydrogen and $R^3$ is selected from the group consisting of chlorine, bromine, fluorine, iodine, methyl, ethyl, methoxy, ethoxy, n-propoxy, iso-propoxy, thiomethoxy, thioethoxy, n-thiopropoxy, and iso-thiopropoxy.

8. The compound of claim 3, wherein $R^3$ is selected from the group consisting of methyl and methoxy.

9. The compound of claim 8, wherein $R^3$ is methyl, $R^4$ is hydrogen, $R^5$ is hydrogen.

10. The compound of claim 8, wherein $R^3$ is methoxy, $R^4$ is hydrogen, $R^5$ is hydrogen.

11. The compound of claim 1 selected from the group consisting of iodoethynyl 4-methylbenzene sulfone; iodoethynyl 4-methoxybenzene sulfone; iodoethynyl 4-thiomethoxybenzene sulfone; iodoethynyl 4-t-butylbenzene sulfone; iodoethynyl 4-ethylbenzene sulfone; iodoethynyl 4-trifluoromethoxybenzene sulfone; iodoethynyl 2,4,6-trimethylbenzene sulfone; iodoethynyl 3,4-dimethoxybenzene sulfone; and iodoethynyl benzene sulfone.

12. Iodoethynyl 4-methylbenzene sulfone.

13. Iodoethynyl 4-methoxybenzene sulfone.

14. Iodoethynyl 4-ethylbenzene sulfone.

15. A compound having the formula

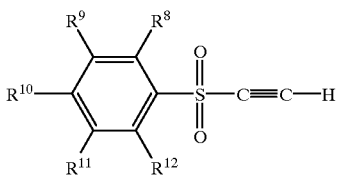

wherein $R^8$, $R^9$, $R^{10}$, $R^{11}$, and $R^{12}$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —$CF_3$, —$OCF_3$, —$NO_2$, acetyl, or —NR$^{13}R^{14}$; $R^{13}$ and $R^{14}$ are independently hydrogen, methyl, or ethyl; and at least one of $R^8$, $R^9$, $R^{10}$, $R^{11}$, and $R^{12}$ is not hydrogen or methyl; with the proviso that $R^{10}$ is fluorine, iodine, substituted or unsubstituted n-propoxy, substituted or unsubstituted iso-propoxy, substituted or unsubstituted linear or branched $C_1$–$C_3$ thioalkoxy, substituted or unsubstituted ethyl, substituted or unsubstituted linear or branched $C_3$–$C_8$ alkyl, hydroxyl, thiol, —CN, —$CF_3$, —$OCF_3$, acetyl, or —$NR^{13}R^{14}$ when $R^8$, $R^9$, $R^{11}$, and $R^{12}$ are hydrogen.

16. The compound of claim 15, wherein $R^8$ and $R^9$ are hydrogen.

17. The compound of claim 16, wherein $R^{10}$ and $R^{11}$ are hydrogen and $R^{12}$ is selected from the group consisting of chlorine, bromine, fluorine, iodine, methoxy, ethoxy, n-propoxy, iso-propoxy, thiomethoxy, thioethoxy, n-thiopropoxy, and iso-thiopropoxy.

18. The compound of claim 16, wherein $R^{10}$ and $R^{12}$ are hydrogen and $R^{11}$ is selected from the group consisting of chlorine, bromine, fluorine, iodine, methoxy, ethoxy, n-propoxy, and iso-propoxy.

19. The compound of claim 16, wherein $R^{11}$ and $R^{12}$ are hydrogen and $R^{10}$ is selected from the group consisting of fluorine, iodine, ethoxy, n-propoxy, iso-propoxy, thiomethoxy, thioethoxy, n-thiopropoxy, and iso-thiopropoxy.

20. The compound of claim 16, wherein $R^{10}$ and $R^{11}$ are methoxy and $R^{12}$ is hydrogen.

21. The compound of claim 15 selected from the group consisting of ethynyl 4-t-butylbenzene sulfone; ethynyl 4-thiomethoxybenzene sulfone; ethynyl 4-ethylbenzene sulfone; ethynyl 4-trifluoromethoxybenzene sulfone; and ethynyl 3,4-dimethoxybenzene sulfone.

22. A compound having the formula wherein $R^8$, $R^9$, $R^{10}$, $R^{11}$, and $R^{12}$ are independently hydrogen or methyl and at least two of $R^8$, $R^9$, $R^{10}$, $R^{11}$, and $R^{12}$ are methyl; with the proviso that $R^8$ is not methyl when $R^9$ and $R^{11}$ are hydrogen and $R^{10}$ and $R^{12}$ are methyl.

23. A composition comprising a compound of claim 1 and a solvent.

24. The composition of claim 23, wherein said solvent comprises water.

25. The composition of claim 24, wherein the concentration of said compound is from about 0.0005 to about 5% by weight based on 100% total weight of composition.

26. The composition of claim 25, wherein the concentration of said compound is from about 0.001 to about 0.1% by weight.

27. A composition comprising a compound of claim 1 and at least one of a surface active agent, wetting agent, adhesive, emulsifier, preservative, filler, carrier, viscosity regulator, pH regulator, binder, tackifier, and fertilizer.

28. A composition comprising a compound of claim 15 and a solvent.

29. The composition of claim 28, wherein said solvent comprises water.

30. The composition of claim 29, wherein the concentration of said compound is from about 0.0005 to about 5% by weight based on 100% total weight of composition.

31. The composition of claim 30, wherein the concentration of said compound is from about 0.001 to about 0.1% by weight.

32. A composition comprising a compound of claim 15 and at least one of a surface active agent, wetting agent, adhesive, emulsifier, preservative, filler, carrier, viscosity regulator, pH regulator, binder, tackifier, and fertilizer.

33. A composition comprising a compound of claim 22 and a solvent.

34. The composition of claim 33, wherein said solvent comprises water.

35. The composition of claim 34, wherein the concentration of said compound is from about 0.0005 to about 0.5% by weight based on 100% total weight of composition.

36. The composition of claim 35, wherein the concentration of said compound is from about 0.001 to about 0.1% by weight.

37. A composition comprising compound of claim 22 and at least one of a surface active agent, wetting agent, adhesive, emulsifier, preservative, filler, carrier, viscosity regulator, pH regulator, binder, tackifier, and fertilizer.

38. A method of preparing a halogenated alkynyl aryl sulfone having the formula

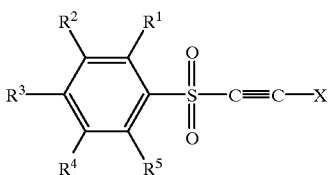

wherein $R^1$, $R^2$, $R^3$, $R^4$, and $R^5$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_3$ thioalkoxy, substituted or unsubstituted linear or branched $C_1$–$C_8$ alkyl, hydroxyl, thiol, —CN, —CF$_3$, —OCF$_3$, —NO$_2$, acetyl, or —NR$^6$R$^7$; $R^6$ and $R^7$ are independently hydrogen, methyl, or ethyl; and X is iodine or bromine, said method comprising the step of reacting (i) an alkynyl aryl sulfone having the formula

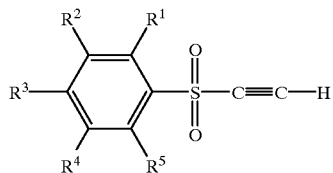

with (ii) N-iodosuccinamide or N-bromosuccinamide, (iii) acetone, and (iv) silver nitrate to yield said halogenated alkynyl aryl sulfone.

39. The method of claim 38, wherein said step comprises reacting (i) a mixture of methanol and a trimethylsilylalkynyl aryl sulfone having the formula

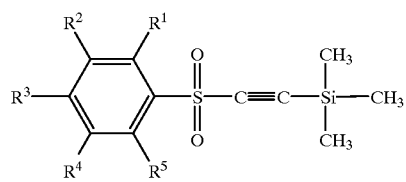

with (ii) a mixture of potassium carbonate and sodium bicarbonate in water to yield the corresponding halogenated alkynyl aryl sulfone.

40. A biocidal composition comprising
   (a) a microbiocidally effective amount of one or more compounds having the formula

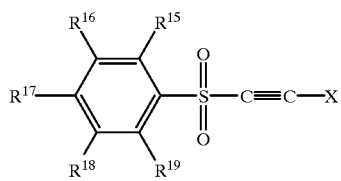

where $R^{15}$, $R^{16}$, $R^{17}$, $R^{18}$, and $R^{19}$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —CF$_3$, —OCF$_3$, —NO$_2$, acetyl, or —NR$^{20}$R$^{21}$; $R^{20}$ and $R^{21}$ are independently hydrogen, methyl, or ethyl; and X is iodine or bromine.

41. A bactericidal composition comprising
   (a) a bactericidally effective amount of one or more compounds having the formula

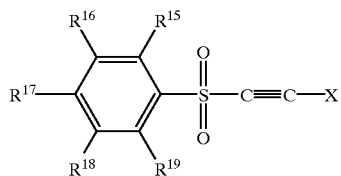

where $R^{15}$, $R^{16}$, $R^{17}$, $R^{18}$, and $R^{19}$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —CF$_3$; —OCF$_3$, —NO$_2$, acetyl, or —NR$^{20}$R$^{21}$R$^{20}$ and $R^{21}$ are independently hydrogen, methyl, or ethyl; and X is iodine or bromine.

42. A fungicidal composition comprising
(a) a fungicidally effective amount of one or more compounds having the formula

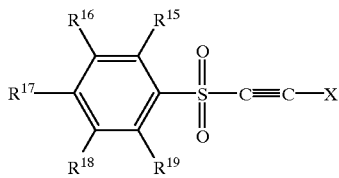

where $R^{15}$, $R^{16}$, $R^{17}$, $R^{18}$, and $R^{19}$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —CF$_3$, —OCF$_3$, —NO$_2$, acetyl or —NR$^{20}$R$^{21}$; $R^{20}$ and $R^{21}$ are independently hydrogen, methyl, or ethyl; and X is iodine or bromine.

43. A method of controlling microorganisms comprising applying a microbiocidally effective amount of one or more compounds having the formula

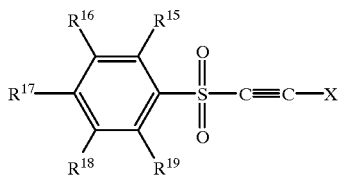

where $R^{15}$, $R^{16}$, $R^{17}$, $R^{18}$, and $R^{19}$ are independently hydrogen, chlorine, bromine, fluorine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, —CN, —CF$_3$, —OCF$_3$, —NO$_2$, acetyl, or —NR$^{20}$R$^{21}$; $R^{20}$ and $R^{21}$ are independently hydrogen, methyl, or ethyl; and X is hydrogen, iodine, or bromine.

44. A method of controlling bacteria comprising applying a bactericidally effective amount of one or more compounds having the formula

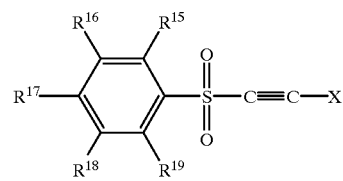

where $R^{15}$, $R^{16}$, $R^{17}$, $R^{18}$, and $R^{19}$ are independently hydrogen, chlorine, bromine, flourine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, -CN, -CF$_3$, -OCF$_3$, -NO$_2$, acetyl, or -NR$^{20}$R$^{21}$; $R^{20}$ and $R^{21}$ are independently hydrogen, methyl, or ethyl; and X is hydrogen, iodine, or bromine.

45. A method of controlling fungi comprising applying a fungicidally effective amount of one or more compounds have the formula

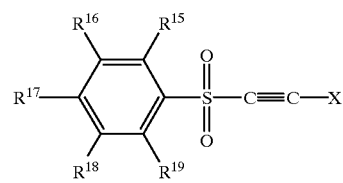

where $R^{15}$, $R^{16}$, $R^{17}$, $R^{18}$, and $R^{19}$ are independently hydrogen, chlorine, bromine, flourine, iodine, substituted or unsubstituted linear or branched $C_1$–$C_3$ alkoxy, substituted or unsubstituted linear or branched $C_1$–$C_3$ thioalkoxy, substituted or unsubstituted linear or branched $C_1$–$C_8$ alkyl, hydroxyl, thiol, -CN, -CF$_3$, -NO$_2$, acetyl, or -NR$^{20}$R$^{21}$; $R^{20}$ and $R^{21}$ are independently hydrogen, methyl, or ethyl, and X is hydrogen, iodine, or bromine.

* * * * *